Figure 1:
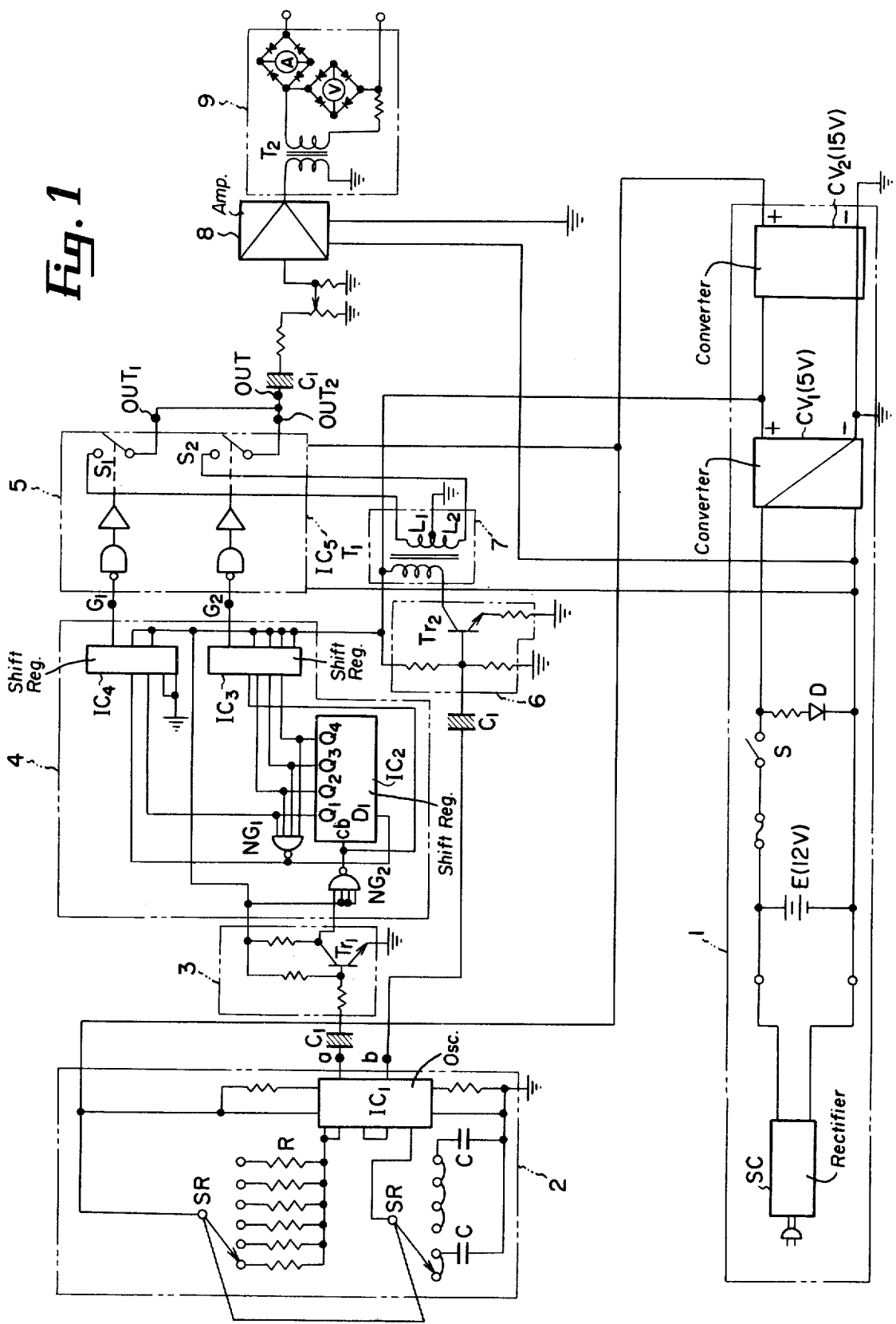

United States Patent [19]
Sato

[11] 3,954,111
[45] May 4, 1976

[54] ELECTRIC THERAPEUTICAL APPARATUS WITH AUDIO FREQUENCY BAND ALTERNATING CURRENT

[76] Inventor: Koh Sato, 14 of 670, Tarumachi, Kohhoku, Yokohama,, Japan

[22] Filed: July 17, 1974

[21] Appl. No.: 489,113

[30] Foreign Application Priority Data
Dec. 28, 1973 Japan............................ 46-2027

[52] U.S. Cl. ............................ 128/419 R; 128/422
[51] Int. Cl.² ........................................ A61N 1/36
[58] Field of Search ............... 128/419 R, 420, 421, 128/422, 423, 2.1 R, 172.1, 1 C

[56] References Cited
UNITED STATES PATENTS

| | | | |
|---|---|---|---|
| 1,764,347 | 6/1930 | Pullwitt............................ | 128/420 |
| 1,908,688 | 5/1933 | Call................................ | 128/421 |
| 3,204,637 | 9/1965 | Frank et al. .................... | 128/423 |
| 3,294,092 | 12/1966 | Landaver........................ | 128/420 |
| 3,791,373 | 2/1974 | Winkler et al.................. | 128/422 |

FOREIGN PATENTS OR APPLICATIONS
380,247   9/1932   United Kingdom................ 128/420

Primary Examiner—William E. Kamm
Attorney, Agent, or Firm—Fidelman, Wolffe & Waldron

[57] ABSTRACT

An electric therapeutical method and apparatus for medically treating diseases caused in the human body by utilizing natural phenomena that organisms including human being endowed with natural curative properties, that alternating current (generally referred to as biological electric current) is found in live cells and that the more active the vital action in cells, the more intensive biological current flows therein, through the introduction of alternating current into affected cells having abnormalities in their functions to activate the vital actions thereof, thereby enhancing the natural curative properties which such cells are originally endowed with.

2 Claims, 2 Drawing Figures

ELECTRIC THERAPEUTICAL APPARATUS WITH AUDIO FREQUENCY BAND ALTERNATING CURRENT

The present invention relates to an electric therapeutical method and apparatus, more particularly to the provision of highly effective electric therapy by periodically providing quiescent periods of a desired duration having a zero potential in alternating electric current of audio frequency band to form therapeutical electric current and then causing the therapeutical electric current to be conducted through the human body.

Hitherto, there have been several kinds of so-called electric therapeutical apparatuses to be used for the medical treatments of headache, stiffness of shoulders, paralysis of peripheral nervous system, insomnia and muscular fatigue due to sports of the like by introducing an electric current into human body from outside. However it has not been generally established yet what kind of action of electric current on the human body can cause such therapeutical effects.

Such conventional examples and experiences in the field tell us in general that, comparing one case in which alternating electric current is conducted through the human body with the other case in which direct electric current (naturally, it has some intermittent wave-form owing to give stimuli in an optional cycle to muscles or nerves for therapeutical purposes) is conducted through the human body, despite of the fact that far greater electric current can be conducted through the human body in a given time without giving any uncomfortable feelings to the patient in the case of alternating current as compared with direct electric current, the conduction of alternating current through the human body brings forth hardly any therapeutical effects, while in the case of direct current, only a small amount of current can be conducted through the human body because of unpleasant stimulus to be caused by the conduction of direct current, although such a small amount is enough to produce therapeutical effects to an extent. Also, it has been said that the human heart is more vulnerable to alternating current than to direct current (the most of electric shock accidents to death in the past have been caused by alternating current).

Therefore, in practically almost all of the existing electric therapeutical apparatuses in use, direct electric current having an intermittent wave-form with fundamental frequencies lower than 50 Hz has been adopted as their therapeutical electric current. In this case, the fundamental frequency means the number of waves generated in a second, but not the one referred to generally in the electric terminology.

In the therapeutical apparatuses (generally, referred to as low frequency electric therapeutical apparatuses) conventionally used, since direct current is adopted as therapeutical electric current, the intensity of the therapeutical electric current has been limited to certain values the miximum of which being in the order of 1 mA at best. Further, despite of such a very limited value of therapeutical electric current, because of the naturally stimulant characteristic of direct current, these conventional electric therapeutical apparatuses have been hardly applicable to the medical treatments of special parts of the human body such as the affected parts of eyes and tongues having very sensitive nerves therein due to uncomfortableness to be caused and scarcely applicable especially to young and old men as well as to valetudinarian who seriously stand in need of this kind of medical treatment. Furthermore, it has not been possible to expect any therapeutical effects higher than a certain level, with the resultant unsatisfactory therapeutical effects, because after all the therapeutical electric current is limited to very small values, and the therapeutical subjects have been necessarily narrowly confined, because the therapeutical process consists merely in the intermittent application of the same form of stimulus onto muscles or nerves.

The present invention overcomes these shortcomings and disadvantages found in the conventional electric therapeutical apparatuses by improving therapeutical effects of direct current and increasing the intensity of the therapeutical electric current in utilization of the characteristic of alternating current that is compratively readily conducted through the human body. Further, according to the present invention, in application of the fact that the conduction of electric current having an alternating current wave-form is found in the human body, the therapeutical electric current is provided with a wave-form of alternating current having a frequency in the audio frequency band and arranged so that quiescent periods of a desired duration having a zero potential occur periodically.

It is therefore a general object of the invention to provide an electric therapeutical method and apparatus in use or the audio frequency band alternating current.

The above and further objects and novel features of the invention will be apparent from the following description of embodiments with reference to the accompanying drawings. It is to be expressly understood, however, that the drawings are for purpose of illustration only and are not intended as a definition of the limits of the invention.

Figure 2:
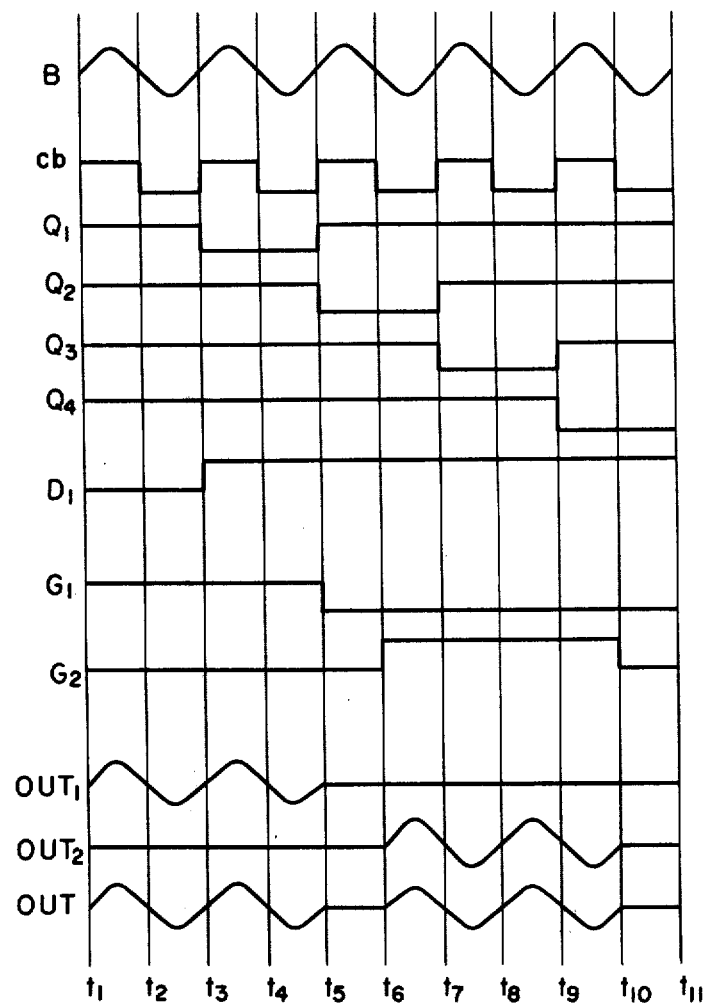

In the drawings:

FIG. 1 is an electric wiring diagram of a preferred embodiment which is designed to acquire a wave-form of therapeutical electric current required in the electric therapeutical apparatus according to the present invention; and FIG. 2 is a chart showing wave-forms of electric current and signals observed at the respective essential parts in the electric wiring diagram as shown in FIG. 1.

Referring now in particular to FIG. 1, an electric therapeutical apparatus of the invention comprises a power supply section 1, an oscillator section 2 connected to the 12 volts output terminal of the power supply section 1, a wave-shaping section 3 to shape one output from the oscillator section 2 having a triangular wave-form (saw-tooth wave-form) into a rectangular wave-form, an arithmetical operation section 4 to produce a quiescent period of a half-cycle duration for every desired number of waves by means of the rectangular wave output from the wave-shaping section 3, an electronic switch section 5 which interrupts the other output from the oscillator section having a sinusoidal wave-form at a predetermined period by means of signals fed from the arithmetical operation section 4, a buffer amplifier section 6 which relays the sinusoidal wave output from the oscillator section 2, a phase inverter section 7 which inverts at a predetermined period the phase of the sinusoidal wave output supplied through the buffer amplifier section 6, namely to shift the phase by 180°, a main amplifier section 8 which amplifies the output from the electronic switch section 5, and in output section 9.

Hereafter, these respective component sections are described sequentially in further detail.

(Power supply section)

The power supply section 1 shown in FIG. 1 is connected to a power source having a commercial frequency and rectifies electric current drawn from the commercial frequency power souce to produce a direct current with the voltage of 12 volts by means of a rectifier circuit SC, which in turn is dropped to 5 volts in voltage and inverted in polarity through a converter $CV_1$ for the purpose of voltage-dropping and inversion, and the resultant output of the converter $CV_1$ is then boosted to a voltage of 15 volts by means of a converter $CV_2$.

The rectifier circuit SC has its positive terminal grounded and has its negative terminal connected to the electronic switch section 5 and to the main amplifier section 8. The converter $CV_1$ has its positive output terminal connected to the phase inverter section 7 and to the arithmetical operation section 4, and the converter $CV_2$ has its positive output terminal connected to the oscillator section 2. In the power supply section 1, E denotes a portable direct current power source such as 12-volt battery, which is preferred to be of a chargeable type. The element D connected in parallel with the input terminals of the converter $CV_1$ is a light-emitting diode which indicates through light-emission that the source switch S is turned on.

(Oscillator section)

The oscillator section 2 comprises, in principle, a RC-oscillation circuit, wherein a rotary switch SR (though the rotary switch SR is shown as if it were composed of two switch sections for the convenience of illustration, it is actually integrated into one switch structure) is operated to change the ratio of the resistance versus the capacitance which are to be connected together through the integration circuit $IC_1$ (generally, the $IC_1$ may be of a type called as "CMOS", i.e. "COS/-MOS" for complementary symmetry metal-oxide-semiconductor) to produce alternating current having a desired frequency at the output terminals $a$ and $b$ of the $IC_1$.

Alternating current output with a triangular waveform is produced at the output terminal $a$ of the $IC_1$ and alternating current output with a sinusoidal wave-form is produced at the output terminal $b$ thereof, respectively.

Wave-shaping section)

This wave-shaping section 3 receives the alternating current output from the output terminal $a$ of the $IC_1$ in the oscillator section 2 through a coupling condenser $C_1$, then amplifies and simultaneously shapes the triangular input to produce an output having a rectangular wave-form, which, in turn, is transmitted to the arithmetical operation section 4.

(Arithmetical operation section)

The arithmetical operation section 4 comprises an $IC_2$ which receives the higher level of the rectangular wave signal as its "on-signal" while the lower level as its "off-signal", and then shifts sequentially the terminal to be turned off at each application of the "on-signal" input (the $IC_2$ is referred to as shift register), $IC_3$ and $IC_4$ which generate output signals for a predetermined time by using signals fed from the shift register $IC_2$ (these $IC_3$ and $IC_4$ are actually integrated into a structure, although many terminals provided in one IC piece are connected according to the manner as shown in the drawing), and a NAND-gate NG which generates predetermined/signals in accordance with the output signals appearing at the terminals $Q_1$, $Q_2$, $Q_3$ and $Q_4$ of the shift register $IC_2$. In the drawing, the NAND-gate NG is shown as being divided into two pieces of $NG_1$ and $NG_2$, although these are actually integrated into one structure. Since the NAND-gate is provided with more number of terminals than required, the required number of terminals are used for the $NG_1$, and the remaining terminals are used for $NG_3$ to invert the phase of the rectangular wave signal applied to the terminal Cb of the $IC_2$.

The $IC_2$ shifts sequentially the terminal to be turned off in the sequence of $Q_1$, $Q_2$, $Q_3$ and $Q_4$ composing the four Q terminals as a whole at each application an on-signal to the Cb terminal, causing the remaining Q terminals all to become off-state. When all of the Q terminals are put into on-condition, an off-signal is supplied to the $D_1$ terminal to put the $D_1$ terminal into off-condition through the action of $NG_1$ connected to the Q terminals. That is to say, only one terminal out of the Q terminals and the $D_1$ terminal of $IC_2$ is always in off-condition, and the remaining terminals are all in on-condition. The $NG_1$ does not generates an off-signal, unless all of the Q terminals are in on-condition, but generates an on-signal whenever any one set of the terminals is in off-condition.

Hereafter, referring now to FIG. 2, the on and off-conditions at the respective terminals are described with reference to the respective input times of the rectangular wave applied to the Gb terminal.

After the time $t_1$ when all of the Q terminals are put into on-condition, if an initial on-signal is applied to the Cb terminal at time $t_3$, the $Q_1$ terminal is put into off-condition at that time and kept in the said condition until the time $t_5$ when the next on-signal is supplied to the Cb terminal. When the $Q_1$ terminal is put into off-condition, all other terminals $Q_2$, $Q_3$, $Q_4$ and the $D_1$ terminal will become on-condition, putting the $D_1$ terminal which was in off-condition into on-condition. If an on-signal is applied to the Cb terminal at the time $t_5$, the off-condition which has been at the $Q_1$ terminal is shifted to the $Q_2$ terminal, and the $Q_1$ terminal goes back to on-condition again. Thereafter, at times $t_7$ and $t_9$, the terminals $Q_3$ and $Q_4$ are put into off-condition, respectively. At the time $t_{11}$, the termiinal $Q_4$ goes back to on-condition, namely all of the Q terminals take on-condition, with the result that the terminal $D_1$ takes off-condition, recovering the same condition as that at the time $t_1$.

Thus, the Q terminals and the $D_1$ terminal of the $IC_2$ shift their conditions from on to off or vice versa at a predetermined timing to form a cycle of a period ranging from the time $t_1$ to $t_{11}$, and this cycle is repeated in the manner as described above.

The $IC_3$ and $IC_4$ arithmetically treat the state signals appearing at the Q terminals and $D_1$ terminal of $IC_2$ to produce desired signals at the output terminals thereof and the $IC_3$ is connected to the terminals $Q_2$, $Q_3$ and $Q_4$ of the $IC_2$, while the $IC_4$ is connected to the terminals $Q_1$ and $D_1$ of the $IC_2$.

The $IC_4$ receives a signal appearing at the $Q_1$ terminal and having a wave-form as shown in FIG. 2 and inverts the signal, and at the same time, it receives a signal appearing at $D_1$ terminal and inverts the polarity thereof. Thereafter, the $IC_4$ adds the resultant signals together to produce a signal at its output terminal $G_1$. That is to say, the signal appearing at the terminal $G_1$ functions as an on-signal during the time between $t_1$ and $t_5$ and an off-signal during the time between $t_5$ and $t_{11}$. In the meantime, the $IC_3$ adds a signal produced by multiplying the inverted signal of the signal appearing at the $Q_2$ terminal by the inverted signal of the rectangular wave signal from the wave-shaping section 3, a signal produced by inverting the signal from the $Q_3$ terminal and a signal produced by multiplying the inverted signal of the signal from the $Q_4$ terminal by the inverted signal of the rectangular wave signal from the wave-shaping section 3 together to produce at the $G_2$ terminal a signal as shown in FIG. 2 at $Q_2$.

The signal appearing at the $G_1$ terminal comprises an on-signal during the time from $t_1$ to $t_5$ and an off-signal during the time from $t_5$ to $t_{11}$. The signal appearing at the $G_2$ terminal is in on-condition only during the time between $t_6$ and $t_{10}$, while in off-condition during the remaining portion in the cycle. Similarly to the on and off-conditions found at the respective terminals of $IC_2$, these two signals appearing at the terminals $G_1$ and $G_2$ both have a cyclic period ranging from the time $t_1$ to $t_{11}$, and this cycle is repeated in the same manner as described above. As clearly understood from the forms of the output signals at the terminals $G_1$ and $G_2$, the oscillator section 2 establishes a time lag corresponding to a half of the cyclic period between the on-signal at the $G_1$ terminal and the second on-signal at the $G_2$ terminal.

(Buffer amplifier section)

The buffer amplifier section 6 shown in FIG. 1 receives the sinusoidal wave output appearing at the $b$ terminal of the oscillator section 2 which has its direct current component removed off through the coupling capacitor $C_1$, and then couples the output to the phase inverter section 7.

(Phase inverter section)

The phase inverter section 7 shown in FIG. 1 comprises a transformer $T_1$ which has its intermediate tap of the secondary winding grounded and receives at its primary winding the output from the buffer amplifier section 6. Then, the inverter section 7 shifts in 180° the phase of the sinusoidal wave signal from the buffer amplifier section 6 by using either one of two partial windings $L_1$ or $L_2$ composing the secondary winding.

(Electronic switch section)

The electronic switch section comprises an integrated circuit $IC_5$ which has a function to close either one circuit of two partial windings $L_1$ or $L_2$ in the phase inverter section 7 or to open both of these two windings $L_1$ or $L_2$ by means of receiving the output signals from the arithmetical operation section 4, namely the signals appearing at the terminals $G_1$ and $G_2$. For example, provided that, referring now to FIG. 1 and FIG. 2, one switch section $S_1$ operated on and off by the signal from the $G_1$ terminal is connected to one partial winding $L_1$ and the other switch section $S_2$ operated on and off by the signal from the $G_2$ terminal is connected to the other partial winding $L_2$, an output having an identical wave-form to the sinusoidal wave signal B appearing at the terminal $b$ appears at the one primary output terminal $OUT_1$ of the electronic section 5 by the action of the partial winding $L_1$ during the time interval from $t_1$ to $t_5$ in which the on-signal appears at the $G_1$ terminal, which an inverted sinusoidal wave signal of the sinusoidal wave signal B appearing at the terminal $b$ appears at the other primary output terminal $OUT_2$ by the action of the partial winding $L_2$ during the period from $t_6$ to $t_{10}$ in which the on-signal appears at the $G_2$ terminal, since the switch $S_2$ of the electronic switch section 5 is turned on during the latter period.

Therefore, electric current having a composite wave-form produced by combining the respective outputs at the primary output terminals $OUT_1$ and $OUT_2$ appeares at the composite output terminal OUT of the electronic switch section 5 during the whole period from $t_1$ to $t_{11}$.

(Main amplifier section)

The main amplifier section 8 as shown in FIG. 1 receives the output current appearing at the composite output terminal OUT of the electronic switch section 5 through a coupling condenser C and amplifies the current to the extent of a level required for the terapeutical purpose.

(Output section)

The output section 9 takes out the output of the main amplifier section 8 as a therapeutical electric current to be used in the therapeutical apparatus according to the present invention, to which output section an ammeter A and a voltmeter V are connected, as shown in FIG. 1.

In actually operating the therapeutical apparatus according to the present invention which has a circuit arrangement as aforementioned, a pair of conduction pads or elements (not shown) connected to the output terminals of the therapeutical apparatus is placed on the affected parts of the human body through the conduction pads to medically treat the affected parts.

In the preferred embodiment, the wave-form of the therapeutical electric current is shown as having a quiescent period corresponding to a half of the cyclic period of the sinusoidal wave between two successive waves in one phase and two successive waves in the opposite phase. However, according to many experimental examples, in considering in terms of the group-wave-form varying in a range from the minimum group composed of one wave in one phase and one wave in the opposite phase adjacent to each other to the maximum group composed of 16 successive waves in one phase and 16 successive waves in the opposite phase immediately following thereto, it is preferred, in order to obtain some significant therapeutical effects, to arrange the wave-form so that the number of waves in one phase is equal to that in the opposite phase or so that the number in one phase is one way more than that in the opposite phase, and especially, the most ideal arrangement of group wave-forms is that in which four successive waves in one phase are followed by three successive waves in the opposite phase. As to the length of quiescent period interposed between the respective group wave-form and producing zero-potential therebetween, according to the therapeutical effects obtained through the actual uses of the apparatus, it is preferred to set the length of the quiescent period to a value in the range from the minimum of half a fundamental cycle (the cycle in the sinusoidal wave) used to the maximum length of 3.5 times of the cycle, and it has been determined that the quiescent time corresponding to the length of half a cycle can be bring forth the highest therapeutical effects, although the length does not have any limiting sense in view of the fundamental idea of the present invention that the quiescent periods having a zero potential are periodically interposed in alternating current to give therapeutical actions in direct current to alternating current which causes generally almost no therapeutical effects. The frequency of the sinusoidal wave appearing at the terminal b of the oscillator section 2 can be chosen to a desired value in the range between the minimum frequency of 250 Hz and the maximum of 6000 Hz.

Further, as to the quiescent period, it is true that, if the quiescent period is set to the length of a half cycle, the highest therapeutical effects will result, but the stimulative action on the human body will become stronger accordingly. Therefore, in actual medical treatments, it is preferable to select a rather longer quiescent period until the affected part becomes familiar with the therapeutical electric current. Similarly, since the lower the fundamental frequency of the therapeutical electric current becomes, the higher and stronger will become the therapeutical effects as well as the stimulative actions on the human body, it is preferred that the medical treatment is performed using a higher frequency at its initial stage. As described above, since the quiescent period and the fundamental frequency have a great influence on the therapeutical effects, the best therapeutical process can be achieved by selecting reasonable values according to the states of the affected parts.

Furthermore, it is preferred that the quiescent period is interposed between the respective group wave-form in such a manner that stimuli are given to the affected parts of the human body in a constant and simple rhythm. Moreover, since the simpler the repeating manner of the group wave-form having an identical form and the quiescent period repeated in the entire therapeutical electric current is, the more amount of electric current can be introduced into the human body without giving uncomfortable feelings thereto, it is preferable to set the durations of the group wave and the quiescent period all to the same lengths, respectively. As to the arrangement and the time interval of the quiescent period, in order to permit the more amount of electric current to be introduced into the human body without uncomfortable stimuli thereto according to the same reason for setting the quiescent period to the same length, and in order to simplify the circuit arrangement of the electric therapeutical apparatus, it is also preferred to arrange the quiescent period so that the period lasts for a multiple time interval of half a cycle starting at a time when the group wave-form has dropped to a zero potential.

The reasons why the electric therapeutic apparatus according to the present invention has great therapeutical effects on many of abnormalities affecting the human body are supposed to consist in the fact that the therapeutical electric current comprises principally alternating current wave, enabling the introduction of the larger amount of electric current into the human body, and that therapeutical effects similar to the effects given by direct therapeutical electric current can be obtained, because of the quiescent period interposed between two successive group wave-forms.

In addition, according to the present invention, since the therapeutical electric current is alternating current which is the same kind as that flowing originally in the human body (biological electric current), but having a larger intensity, it can be supposed that the therapeutical electric current acts on the human body in such manner that the vitality of normal cells in the affected part of the human body are improved, but not obtaining the therapeutical effects by merely giving physical stimuli onto the affected part, as seen in the conventional electric therapeutic apparatuses. Also, since the fundamental frequency of the therapeutical electric current falls in the audio frequency band which can be sensed by the human body as an organism, it is supposed that the therapeutical electric current can be introduced into the human body naturally, causing some effects that act to improve the vitality of normal cells.

Next, some remedial or clinical cases by means of the therapeutical apparatus according to the invention are described for the purpose of exemplification.

Case 1: Woman 68 years old, affected by lumbago.

She had been feeling a pain at her loin since about 1 month before, especially severely in walking, but no abnormalities were recognized at her bone or other tissues even by X-ray examination.

By using therapeutical electric current having a frequency of 3000 Hz and intensitiy of about 30 mA from the beginning treatment, she was treated three times in 6 days (20 to 30 minutes of conduction for one treatment) by placing conduction pads elements of 9 × 12 cm on her abdomen and loin, to remove the pain. The pain did not recurred even after 40 days from the final treatment.

Case 1: Woman 36 years old, affected by water-eczema.

Cuticle was exfoliated partially at the affected parts between the first and second toes and between the fourth and fifth toes of her both feet.

By using therapeutical electric current having a frequency of 600 Hz and intensity of 20 to 30 mA, she was treated 5 times in 14 days with 20 to 30 minutes of conduction for each treatment, to remove her self-conscious symptoms, with the result that such symptom did mot recurred even after 30 days from the final treatment.

Case 3: Woman 41 years old, affected by water-eczema.

She had a light inflammation between the first and second toes of her right foot and had exfoliations among almost all toes of both feet.

By using therapeutical electric current having a frequency between 600 and 3000 Hz and intensity of 25 to 30 mA, she was treated by 5 times in 12 days with 20 to 30 minutes of conduction for each treatment, and immediately after the first treatment, her self-conscious symptom was expelled, but itching recurred on the next day. However, the subjective conscious symptom was expelled completely after the second conduction of thereapeutical current, never recurring even after 40 days from the final treatment.

In the above-mentioned two clinical cases of water-eczema, both feet were dipped in lukewarm water to the level of her ankles at a mild temperature, and a pair of conduction pads of 11 × 20 cm were dipped in the container with the lukewarm water in front and in rear to conduct electric current therein. In these cases, it is likely to be preferable to set the fundamental frequency of the therapeutic electric current to a reasonable value in the range between 3000 and 600 Hz according to the preference of the patient. Since the affected parts are not familiar with the therapeutical elecric current at the beginning treatment it is natural that the therapeutic electric current is small and the fundamental frequency is high, but there is a tendency that intensity of the therapeutic electric current becomes higher and the fundamental frequency becomes lower, as the affected parts becomes more familiar with the therapeutical electric current.

Case 4: Woman 63 years old, affected by chronic cholecystitis.

She has been subjected to a decrease of appetite and a disgust against fatty foods with a notable complaint about an oppressing sensation at the solar plexus and had been advised to undergo an operation from a university hospital.

One conduction element of 11 × 13 cm was placed to cover about one-third of the right hypochondrium and the other of the same size was placed on the back to treat her by conducting the therapeutical electric current having a frequency of 3000 Hz and intensity of 20 to 35 mA. Thereafter, the latter conduction element on the back was moved to the loin and the other element of the solar plexus was replaced by another one with the size 5 × 8 cm, and then the therapeutical electric current was changed to about 12 mA. 24 times of 20 to 30 minutes of conduction were performed in 90 days, to alleviate the self-conscious symptom in a week after the beginning treatment. After about one week of treatment, it became possible for her to intake fatty foods. Thereafter, 8 times of treatment for 120 days were given to her, in which the symptom did not recurred.

Case 5: Boy 8 years old, affected by allergic nasal inflammation.

Subjected to "nasal clogging", he had been inhaled a medicine into nostrils 3 times a day, namely before sleeping, midnight, and toward morning to expel his self-conscious symptom in vain.

By calling one conduction element of 14 × 17 cm on the crest and the other of 2.5 × 3.5 cm around the nasal bone, the therapeutical electric current having a frequency of 3000 Hz and an intensity of 3 to 5 mA was conducted therethrough for 20 to 30 minutes twice a week at the beginning. In this manner, he was treated 14 times in 40 days, to expel the necessity of medicine inhalation and self-conscious symptom in about one month. The symptom did not recurred even after 30 days from the final treatment.

Case 6: Woman 31 years old, affected by corns.

She had been subjected to an unbearable pain in keeping standing or walking for successive 30 minutes or so.

By placing conduction elements of 9 × 12 cm on the soles of both feet, the therapeutical current having a frequency of 3000 Hz and intensity of 2 mA was conducted at the beginning. At that time, she felt a sharp stab of an acquate pain at the diseased parts so that is was only possible to increase the therapeutcal current up to 3 mA even after 20 minutes from the start of conduction. However, it became possible to increase gradually the therapeutical current after repeating the treatments 12 times in such manner. In the 15th treatment or so, 8 to 10 mA of therapeutical electric current was possible to be conducted and the irritative pain was remarkably alleviated. Under these conditions, 18 times of 20 to 30 minutes of conductions were given to her in total in 45 days, to expel the self-conscious symptom (no pain occurred in walking for a long time), and the symptom did not recurred even after 30 days from the final treatment.

Besides the above-mentioned remedial cases, there are many more clinical cases which were successfully treated by using the therapeutical apparatus according to the present invention. Among such cases the following diseases are remarkable: toothache, pyrrhea, arthritis, sprain, gynecological disease, hemorrhoids, proctocele, gastroenteric disease, chronic constipation, ozena, chronic tympanitis, stiffness of shoulders, chronic nephritis (the self-conscious symptom decreases gradually without changes in diagonostic observation on urine; that is to say, the self-conscious symptoms such as systemic fatigue or boredom, headache, lumbago, poor appetite or the like are expelled completely).

As described herein above, in addition to the advantage that far superior therapeutical effects can be achieved and remarkably wider range of curable diseases can be covered as compared with the conventional electric therapeutic apparatuses, the following advantages are provided by the electric therapeutical apparatus according to the present invention:

a. Pains and itches to be caused by direct electric current in the conventional therapeutic apparatuses are completely expelled;

b. Besides the privation of pains and itches as described in the above item a), due to the lack of polarizing action (i.e., phenomena causing troubles or irregularities such as burn of the skin, closing of a sweat-gland, dry and rough of the skin, or the like, owing to the difference of current density within the parts of the skin on which the conduction pads contact), there are no probabilities to cause burn and so on, even when the conduction pads are directly contacted with the skin of a patient;

c. Because it is not necessary to take account of the polarizing action, the medical treatment can be effected by merely determining the region suspectable to embrace the disease, applying one conduction pad thereon, and placing the other pad of similar sizes to the former one on the body in such a manner that the body is put therebetween;

(Namely, the handling of the conduction elements and the therapeutical procedures are remarkably simplified and secured due to the advantages as described in the items (a), (b) and (c) and further because the use of alternating current eliminates the necessity to check the polarity of the conduction elements.)

d. Even the affected parts having a trauma on the skin such as water-eczema can be treated, because the therapeutical electric current hardly cause pain (except for fresh traumas such as incised wound; the conventional electric therapeutic apparatuses using direct current give fierce pain to traumas, making it impossible to treat such a trauma);

e. A long time use of the therapeutical apparatus according to the present invention does not cause dry and rough of the skin (due to the clogging of sweetglands inhibiting the perspiration) on which the conduction elements are placed, quite differing from the conventional electric therapeutic apparatuses.

Furthermore, despite of the fact that, the intensity of the therapeutical electric current which can be conducted through the human body varies according to the respective individuals as well as the respective regions of the human body, the electric therapeutical apparatus according to the present invention enables earlier discoveries of any diseases potentially existing in the human body, because the upper limit of such intensity is far smaller in the affected parts than in the sound parts, as clearly described in the above-mentioned clinical cases, and because pains to be caused by such a slight electric current are indicating the existence of some diseases in that part of the human body.

This means that the user of the therapeutical apparatus according to the present invention can control his own health easily by knowing beforehand the intensity of the therapeutical electric current that can be conducted through the respective parts of his body at the normal conditions thereof.

As clearly understood from the above description, the present invention provides a novel electric therapeutical apparatus, wherein alternating current is used as its therapeutical electric current, and which gives considerably high therapeutical effects and actions which are effective to a wider range of deseases as compared with the conventional electric therapeutic apparatuses using direct current as their therapeutical current. Therefore, according to the present invention, because of the use of alternating therapeutical electric current, uncomfortable stimuli such as pains and itches as well as the clogging of sweet-glands are eliminated almost completely and there are no possibilities of remedial accidents owing to any inverse installation of a pair of conduction elements that is probable in alternating current, making the remedial procedure simpler and safer.

Moreover, the therapeutical apparatus according to the present invention is also applicable, because of extremely weak stimuli to the human body, to the medical treatments of babies, infants, valetudinarians and those who have specially sensitive skins to which the conventional electric therapeutic apparatuses have not been applicable. Another application or advantage of the therapeutical apparatus according to the present invention is that the apparatus permits some deseases to be discovered early.

What is claimed is:

1. An electric therapeutical apparatus for treating cells in a human body comprising:
   a pair of means for transmitting a current to a human body; and
   means electrically connected to said transmitting means for producing said current as at least two identical groups of alternating current wave-forms separated by a period of zero amplitude, each of said groups of wave-forms being a continuous sinusoidal wave-form having a fundamental frequency selected from audio frequencies ranging between 250 and 6000 Hz at voltages within $\pm$ 300$^v$ and being not more than about 50 mA, each group of wave-forms not to exceed sixteen full cycles and may be a half a cycle less than a full cycle, said period of zero amplitude being in the range of one half the period of a cycle of said sinusoidal wave-form to three and one half times the period of a cycle of said sinusoidal wave-form.

2. A method for increasing the vitality of cells in a human body comprising:
   producing a current having two identical groups of alternating current wave-forms separated by a period of zero amplitude, each of said groups of wave-forms being a continuous sinusoidal wave-form having a fundamental frequency selected from audio frequencies ranging between 250 and 6000 Hz at voltages within $\pm$ 300$^v$ and being not more than about 50 mA, each group of wave-froms not to exceed sixteen full cycles and may be a half a cycle less than a full cycle, said period of zero amplitude being in the range of one half the period of a cycle of said sinusoidal wave-form to three and one half times the period of a cycle of said sinusoidal wave-form; and
   applying said current to the human body.

* * * * *